(12) United States Patent
Lee

(10) Patent No.: US 8,359,088 B2
(45) Date of Patent: Jan. 22, 2013

(54) FOLDER-TYPE PORTABLE ELECTROCARDIOGRAM MONITOR

(75) Inventor: Sang-Hun Lee, Yongin-si (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 1001 days.

(21) Appl. No.: 12/211,285

(22) Filed: Sep. 16, 2008

(65) Prior Publication Data

US 2009/0112112 A1   Apr. 30, 2009

(30) Foreign Application Priority Data

Oct. 24, 2007   (KR) .......................... 10-2007-0107192

(51) Int. Cl.
*A61B 5/04* (2006.01)
(52) U.S. Cl. ........................................................ 600/509
(58) Field of Classification Search .................. 600/508, 600/509, 372–374, 382, 393; 607/142, 152
See application file for complete search history.

(56) References Cited

U.S. PATENT DOCUMENTS

| | | | | |
|---|---|---|---|---|
| 4,513,753 A | * | 4/1985 | Tabata et al. | 600/519 |
| 4,602,640 A | * | 7/1986 | Wada et al. | 600/395 |
| 5,505,202 A | * | 4/1996 | Mogi et al. | 600/390 |
| 6,486,779 B1 | * | 11/2002 | Alroy | 340/568.7 |
| 6,544,189 B2 | * | 4/2003 | Watrous | 600/528 |
| 7,197,351 B2 | * | 3/2007 | Umeda et al. | 600/393 |
| 7,266,405 B1 | * | 9/2007 | Alroy et al. | 600/386 |
| 2003/0097078 A1 | * | 5/2003 | Maeda | 600/509 |
| 2003/0187363 A1 | * | 10/2003 | Alroy | 600/509 |
| 2005/0277872 A1 | * | 12/2005 | Colby et al. | 604/67 |

FOREIGN PATENT DOCUMENTS

JP   11042214 A   *   2/1999

* cited by examiner

*Primary Examiner* — Eric D. Bertram
*Assistant Examiner* — Elizabeth K So
(74) *Attorney, Agent, or Firm* — Cha & Reiter, LLC

(57) ABSTRACT

A portable electrocardiogram monitor includes: an upper housing and a lower housing coupled to each other via a hinge; and a positive electrode formed on lateral sides of the upper and lower housings, which are disposed opposite sides centering on the hinge.

17 Claims, 4 Drawing Sheets

FOLDER-TYPE PORTABLE ELECTROCARDIOGRAM MONITOR

CLAIM OF PRIORITY

This application claims the benefit under 35 U.S.C. §119 (a) of an application entitled "Folder-type Portable Electrocardiogram Monitor" filed in the Korean Intellectual Property Office on Oct. 24, 2007 and assigned Serial No. 2007-107192, the contents of which are hereby incorporated by reference in their entirety.

BACKGROUND OF THE INVENTION

1. Field of the Invention

The present invention relates to an electrocardiogram, and in particular to a new construction of a folder-type portable electrocardiogram monitor.

2. Description of the Related Art

Electrocardiogram is a medical method for determining whether there is an abnormality in heart function by monitoring a weak electric signal of a living body occurring when the heart contracts and relaxes. A conventional electrocardiogram monitor is an apparatus for monitoring a living body's electric signal related to the activity of a heart. This is performed by contacting electrodes to a body of a person to be monitored in terms of the activity of the heart.

When arranging electrodes, a total of twelve standard limb leads designed by Einthoven, i.e. three standard limb leads, three unipolar limb leads, and six precordial leads, are arranged on the arms, the legs, and an area surrounding the heart of a patient. To record a more precise diagnosis, fifteen to eighteen electrodes may be arranged. In general, for an electrocardiogram examination it is necessary to go to a hospital or medical office, which is troublesome. Therefore, there is an increasing demand for portable electrocardiogram monitors which allow an individual to simply and conveniently conduct daily electrocardiogram monitoring. Some medical machine manufacturers, including Omron, have provided a market with related portable products.

Since employing an arrangement of twelve or more electrodes in a portable electrocardiogram monitor is not practical, a single electrode of lead-I or lead-II is used among the limb leads. Many kinds of arrhythmia diagnoses can be conducted with a single electrode signal. Considering the convenience and ergonomics of the above-mentioned monitoring, it is suitable to position a positive (+) electrode at an edge of the monitor.

An electrocardiogram monitor includes an electrode and a filtering and amplifying means in order to detect a weak signal of a living body. In particular, in a miniaturized portable electrocardiogram monitor, to obtain a good waveform it is necessary to form a contact area of an electrode as wide as possible so as to minimize contact impedance in relation to a body of an individual to be monitored.

FIG. 1 shows a prior art portable electrocardiogram monitor. Referring to FIG. 1, the prior art portable electrocardiogram monitor 100 includes a monitor button 120, a ground electrode 130 (negative (−) electrode), a positive electrode 140, and an image display 110 for displaying a monitored result to a user.

The prior art portable electrocardiogram monitor 100 can monitor an electrocardiogram by pushing the monitor button 120 while the index finger of the user's right hand or the like is in contact with the ground electrode 130 and while the positive electrode 140 positioned at the opposite side is being retained in contact with the user's another body part, such as the left area of the chest, an arm, or the like. The monitored electrocardiogram waveform can be provided to the user through the image display means 110.

The above-mentioned portable electrocardiogram monitor 100 requires electrodes having a wide area to be in contact with the user's body so as to minimize the impedance, thereby obtaining a good waveform.

In particular, the portable electrocardiogram monitor 100 of FIG. 1, has a shape in which the thickness of the monitor increases toward the positive electrode 140 so as to maximize the area of the electrode to be contacted with the user's body.

Therefore, the prior art portable electrocardiogram monitor has a problem in that its thickness and volume are relatively large in order to retain the wide electrode, which affords a limitation in both portability and storage of the portable monitor.

SUMMARY OF THE INVENTION

Accordingly, the present invention has been made to solve the above-mentioned problems occurring in the prior art, and the present invention provides a portable electrocardiogram monitor capable of minimizing a drop in electrocardiogram signal by employing an electrode designed to provide a wide contact area while retaining the slim design and portability.

According to an aspect of the present invention, there is provided a folder-type electrocardiogram monitor including: an upper housing and a lower housing coupled to each other via a hinge; and a positive electrode formed on lateral sides of the upper and lower housings, which are disposed opposite sides centering on the hinge. The opposed adjacent lateral sides are provided with a positive (+) electrode, which is exposed when the monitor is folded, whereby it is possible to provide an electrode area which is wider than that of the conventional electrocardiogram monitor.

BRIEF DESCRIPTION OF THE DRAWINGS

The above features and advantages of the present invention will be more apparent from the following detailed description taken in conjunction with the accompanying drawings, in which.

DETAILED DESCRIPTION OF THE INVENTION

Figure 1:
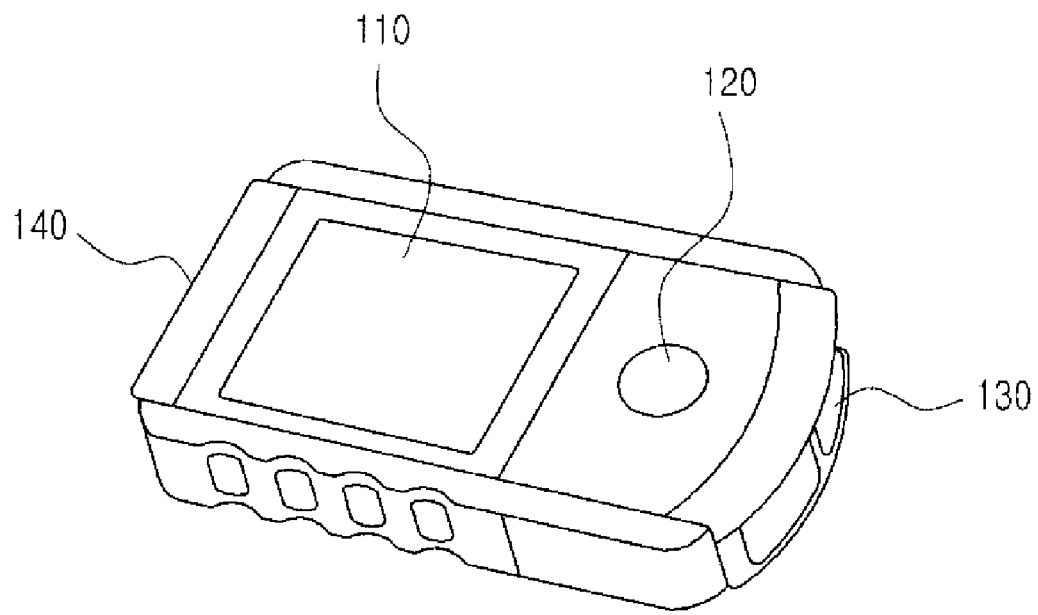
FIG. 1 is a perspective view showing a conventional portable electrocardiogram monitor.

Hereinafter, an exemplary embodiment of the present invention will be described with reference to the accompanying drawings. It should be noted that in the following description, the same elements will be designated by the same reference numerals even though they are shown in different drawings. For the purposes of clarity and simplicity, a detailed description of known functions and configurations incorporated herein may be omitted for conciseness when their inclusion would obscure appreciation of the subject matter of the present invention by a person of ordinary skill in the art.

Figure 2:
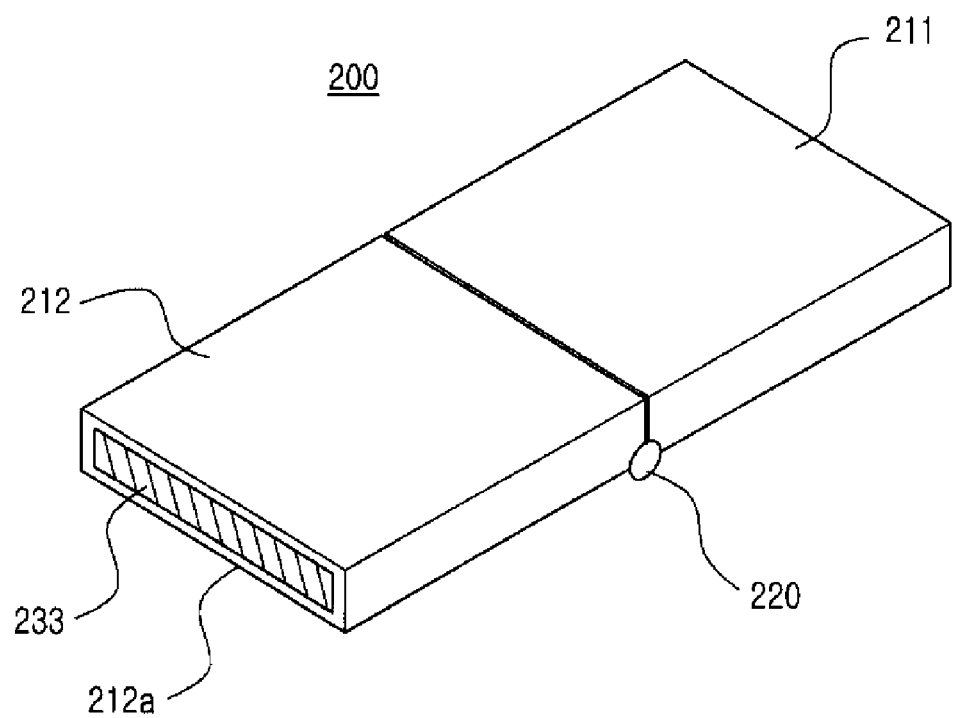
FIG. 2 is a perspective view showing a portable electrocardiogram monitor according to an embodiment of the present invention in an extended state for carrying.
Figure 3:
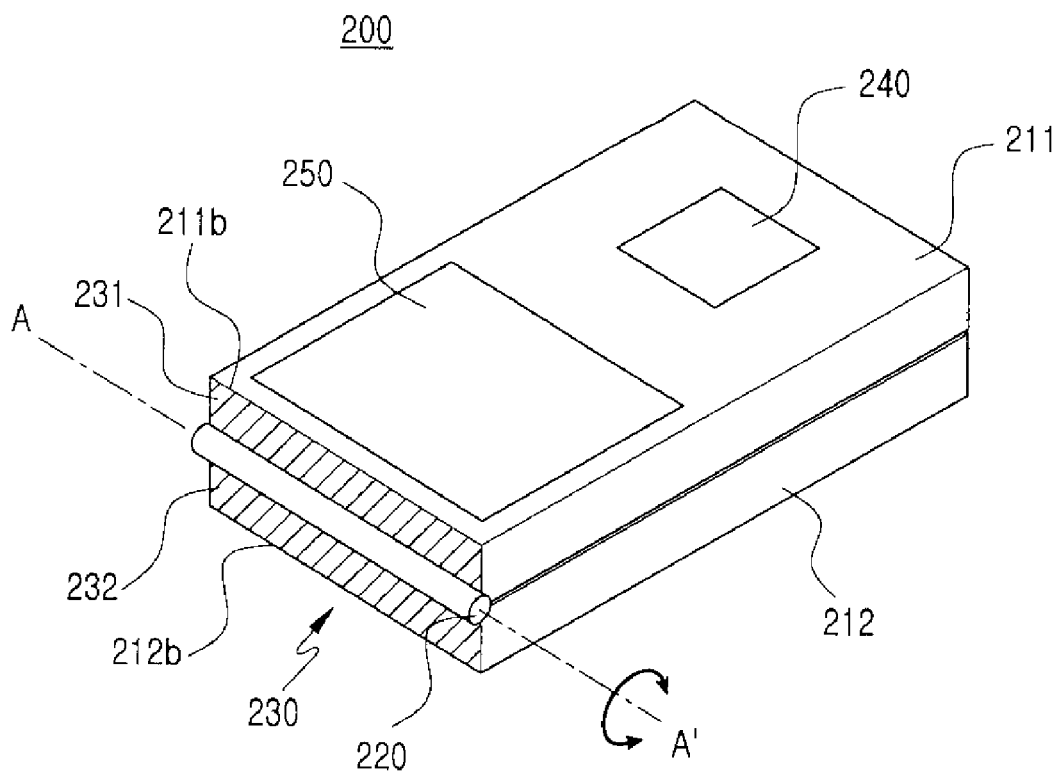
FIG. 3 is a perspective view showing the portable electrocardiogram monitor of FIG. 2 in a folded state for monitoring.

FIG. 2 is a perspective view showing a portable electrocardiogram monitor according to an embodiment of the present invention in an extended state for carrying, and FIG. 3 is a perspective view showing the portable electrocardiogram monitor of FIG. 2 in a folded state for measuring. Referring to FIGS. 2 and 3, the portable electrocardiogram monitor 200 includes: a hinge 220; upper and lower housings 211 and 212 (upper and lower refer to housings when viewed in the folded state as shown in FIG. 3); a positive (+) electrode 230 formed on one lateral side 211b and 212b of each of the upper and lower housings 211 and 212, the lateral sides 211b and 212b being opposed to each other with reference to the hinge, and substantially flush with each other when the monitor is folded as shown in FIG. 3; an image display 250 formed on the upper side of the upper housing 211; a monitor button 240 formed on a part of the upper side of the upper housing 211; and a ground electrode 233 formed on each of the other lateral sides 211a and 212a of the upper and lower housings 211 and 212 opposite to the lateral sides 211b and 212b of the upper and lower housings 211 and 212, on which the positive electrode 230 is formed.

The image display 250 may include an organic liquid crystal display, or any other type of display known to one of skill in the relevant art.

The upper and lower housings 211 and 212 are coupled to each other to be capable of rotating (being collapsed or folded) about the axis A-A' of the hinge 220. When the user carries the monitor 200, the upper and lower housings 211 and 212 are retained in the extended state as shown in FIG. 2. When the user uses the monitor 200, it is folded into two so that the upper and lower housings 211 and 212 are positioned as shown in FIG. 3.

The positive electrode 230 in the folded state as shown in FIG. 3 can be exposed with an exposed area corresponding to a multiple, i.e., two times, the cross-sectional area of the monitor 200 in the extended state as shown in FIG. 2. Therefore, when not used, the portable electrocardiogram monitor 200 has a relatively thin thickness and can be easily carried. When used, the portable electrocardiogram 200 provides a sufficiently wide positive electrode 230 to the user, thereby enabling improved monitoring of an electrocardiogram signal.

The hinge 220 may be formed from a conductive material or may be coated with a conductive material at least at a portion of which is in contact with each of the opposed lateral sides 211b and 212b of the upper and lower housings 211 and 212. This structure enables the hinge 220 to form the positive electrode 230 together with the conductive materials 231 and 232 coated on the opposed lateral sides 211b and 212b of the upper and lower housings 211 and 212.

The positive electrode 230 may be formed from stainless steel, brass, copper or any other metallic material or alloy with low electric resistance, and may be plated, coated or attached to the opposed lateral sides 211b and 212b of the upper and lower housings 211 and 212 opposed to each other with reference to the hinge 220. In addition, the positive electrode 230 and the ground electrode 233 may be both embossed or formed with grooves so as to increase their surface areas to be contacted with the user's body.

When not in use, the inventive portable electrocardiogram monitor 200 can be carried in the state in which the upper and lower housings 211 and 212 are substantially extended as shown in FIG. 2. However, when in use, the portable electrocardiogram monitor 200 is folded so that the upper and lower housing 211 and 212 are positioned as shown in FIG. 3, thereby allowing the positive electrode 230 to be used for electrocardiogram monitoring.

That is, when not used, the portable electrocardiogram monitor 200 can be carried with a thickness corresponding to a fraction, i.e., one half, of the thickness in a state of use. When used, it is possible to provide a positive electrode 230 with an area corresponding to a multiple, i.e., two times, of the area in its unused state.

The folder-type portable electrocardiogram monitor 200 can be used for monitoring an electrocardiogram. If desired, the electrocardiogram monitor may be provided with various additional living body signal measuring sensors known to one of skill in the art.

It is also possible to arrange one or more rows of LED sensors for photo plethysmogram on the opposed lateral sides 211a and 212b of the upper and lower housings 211a and 212a instead of the ground electrode, and to form the monitor button 240 from a conductive material, thereby providing both functions of the ground (or negative (−)) electrode and the button. If so, it is possible to further measure PWV (Pulse Wave Velocity) which is an index of arteriosclerosis. The method of estimating PWV using an electrocardiogram and photo plethysmogram are well known.

Figure 4:
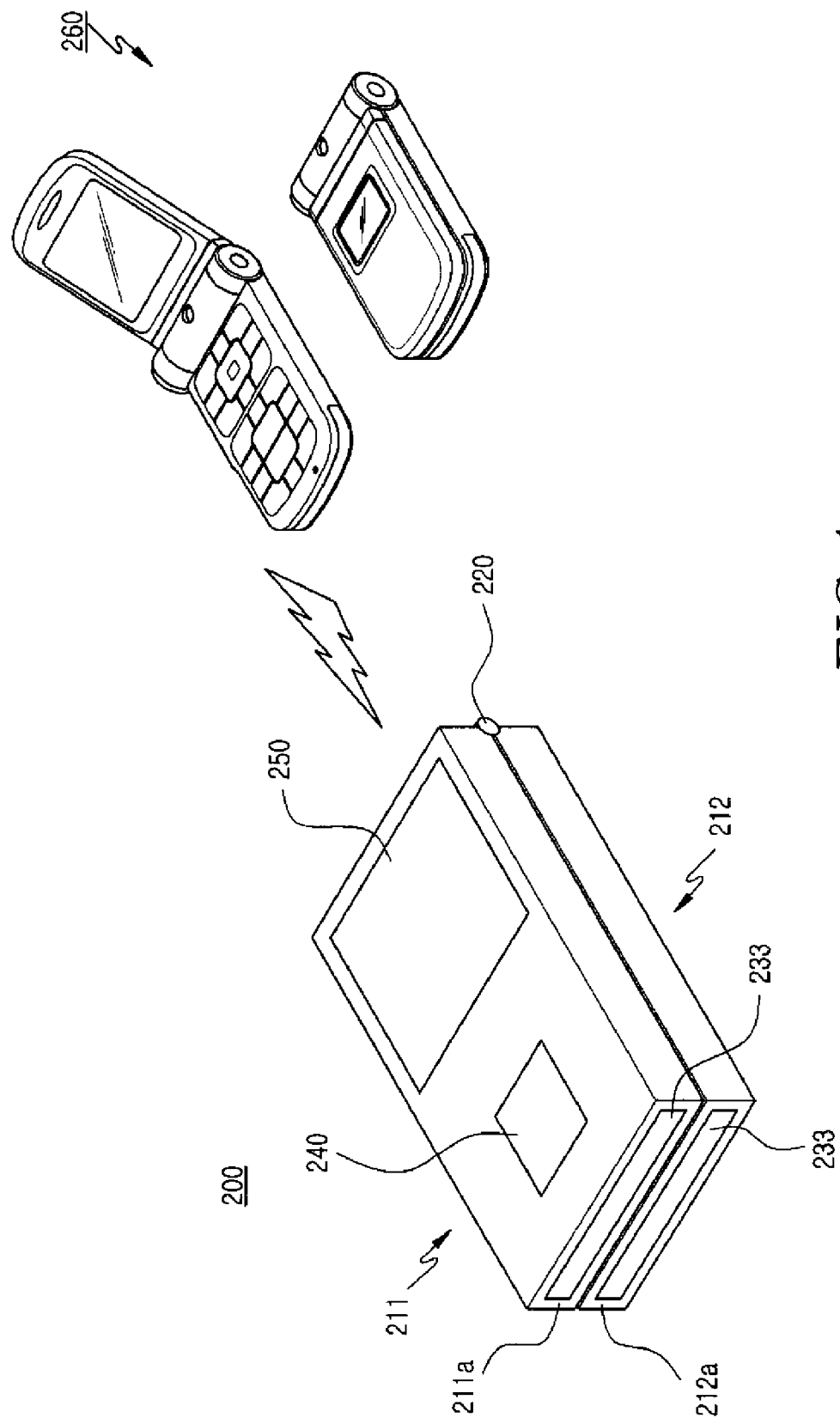
FIG. 4 is a perspective view showing the portable electrocardiogram monitor of FIG. 3 in another direction.

Referring to FIG. 4, the electrocardiogram monitor 200 is capable of being applied to measure the thickness of subcutaneous fat, analyzing body fat, or measuring an melanin index of skin. In addition, by providing a short distance communication means, such as, for example, Bluetooth or Zig-Bee, instead of or along with the image display means 250, it is possible to provide a measured or monitored result to the user through counterpart portable digital apparatuses 260 or an electronic device capable of providing and/or transmitting (i.e., wirelessly) image information.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A portable electrocardiogram monitor comprising:
   an upper housing and a lower housing coupled to each other; and
   a single positive electrode formed on lateral sides of the upper and lower housings and formed as first and second electrode portions which are electrically connected with each other in each of a folded state and an extended state of the upper and lower housings,
   wherein the upper and lower housings unfold into the extended state, and the first and second electrode portions face each other in the extended state at a central region of the monitor, and
   wherein the upper and lower housings fold into the folded state, with the first and second electrode portions juxtaposed with each other and lying in the same plane on one side of the upper and lower housings in the folded state to present the single positive electrode with a substantially continuous surface area comprising the first and second electrode portions.

2. The portable electrocardiogram monitor as claimed in claim 1, further comprising:
   a display formed on an upper side of the upper housing; and
   a monitor button formed on a part of the upper side of the upper housing.

3. The portable electrocardiogram monitor as claimed in claim 1, wherein the first electrode portion of the positive electrode is formed on the lateral side of the upper housing and the second electrode portion of the positive electrode is formed on the lateral side of the lower housing, and wherein the first and second portions of the positive electrode are electrically connected with each other through a hinge for coupling the upper and lower housings to each other.

4. The portable electrocardiogram monitor as claimed in claim 3, wherein the hinge comprises a conductive material.

5. The portable electrocardiogram monitor as claimed on claim 1, wherein the positive electrode comprises stainless steel, brass or copper.

6. The portable electrocardiogram monitor as claimed in claim 2, wherein the image display comprises an organic liquid crystal display.

7. The portable electrocardiogram monitor as claimed in claim 1, wherein a surface of the positive electrode is embossed or formed with grooves.

8. The portable electrocardiogram monitor as claimed in claim 1, further comprising:
a wireless communication means; and
a monitor button formed on a part of an upper side of the upper housing.

9. The portable electrocardiogram monitor as claimed in claim 2, wherein the monitor button comprises a conductive material.

10. The portable electrocardiogram monitor as claimed in claim 3, wherein the hinge operates to fold the upper housing and the lower housing into the folded state such that the positive electrode is substantially exposed.

11. The portable electrocardiogram monitor as claimed in claim 3, wherein the hinge operates to unfold the upper housing and the lower housing into the extended state such that the positive electrode is substantially hidden.

12. The portable electrocardiogram monitor as claimed in claim 10, wherein the upper housing and the lower housing are substantially flush in the folded state of the upper and lower housings.

13. The portable electrocardiogram monitor as claimed in claim 11, wherein the positive electrode in the folded state has an area corresponding to a multiple of the cross-sectional area of the electrocardiogram monitor in the extended state of the monitor in the unfolded state of the upper and lower housings.

14. The portable electrocardiogram monitor as claimed in claim 12, wherein the positive electrode has a surface area substantially corresponding to two times the cross-sectional thickness of the electrocardiogram monitor in the folded state of the upper and lower housings.

15. The portable electrocardiogram monitor as claimed in claim 3, wherein the lateral sides of the upper and lower housings are opposite sides centering on the hinge, so that the first and second electrode portions are positioned directly opposed to each other and in two parallel planes when the upper and lower housings are unfolded, and the first and second electrode portions are positioned adjacent one another and in substantially a single plane when the upper and lower housings are folded.

16. The portable electrocardiogram monitor as claimed in claim 15, where during the folded state of the monitor the hinge causes the positive electrode to be exposed and the portable electrocardiogram monitor operable to provide an electrocardiogram measurement, and during the extended state of the monitor, the hinge causes the positive electrode to not be exposed, and the portable electrocardiogram monitor inoperable to provide an electrocardiogram measurement.

17. The portable electrocardiogram monitor as claimed in claim 15, where a ground electrode is disposed on a lateral side of at least one of said upper and lower housings which is directly opposite the lateral sides on which said positive electrode is disposed.

* * * * *